United States Patent [19]

Schulman et al.

[11] 4,237,900
[45] Dec. 9, 1980

[54] IMPLANTABLE CALIBRATION MEANS AND CALIBRATION METHOD FOR AN IMPLANTABLE BODY TRANSDUCER

[75] Inventors: Joseph H. Schulman, Los Angeles; Douglas G. Ritchie, Pasadena, both of Calif.

[73] Assignee: Pacesetter Systems, Inc., Sylmar, Calif.

[21] Appl. No.: 12,142

[22] Filed: Feb. 14, 1979

[51] Int. Cl.³ .................................................. A61B 5/00
[52] U.S. Cl. ..................................... 128/630; 128/673; 128/736; 128/903
[58] Field of Search ............... 128/630, 631, 632, 672, 128/673, 675, 692, 736, 748, 900, 903

[56] References Cited

U.S. PATENT DOCUMENTS

| | | | |
|---|---|---|---|
| 3,231,834 | 1/1966 | Watanabe | 128/631 |
| 3,717,140 | 2/1973 | Greenwood | 128/706 |
| 3,972,320 | 8/1976 | Kalman | 128/903 |
| 4,127,110 | 11/1978 | Bullara | 128/903 |

OTHER PUBLICATIONS

Barbaro et al. "Medical & Biological Engineering" vol. 17, No. 1, pp. 81-86, Jan. 1979.

*Primary Examiner*—William E. Kamm
*Attorney, Agent, or Firm*—Freilich, Hornbaker, Wasserman, Rosen & Fernandez

[57] ABSTRACT

An implantable body transducer having a self-contained calibration means. An exemplary embodiment comprises an implantable body pressure measuring transducer utilizing an L-C oscillator having a resonant circuit comprising a fixed L and a variable C, the variable C having a fixed capacitive electrode and a movable capacitive electrode in the form of a stiff pressure responsive diaphragm, the output frequency of the oscillator being a function of the pressure sensed by the diaphragm. The transducer incorporates a self-contained calibration means which contains predetermined calibration data with respect to the variable C. The predetermined calibration data is stored in a plurality of PROM storage elements which are sequentially addressed in accordance with the output of a counter, the PROM storage elements providing a serial bit stream which can be used to pulse-code modulate the L-C resonant circuit output. Specific calibration parameters for the variable C are determined during manufacture of the pressure measuring transducer. These parameters are programmed into the digital storage elements of the PROM, burned in, and then utilized to modulate the resonant circuit output subsequent to implantation in a body. In addition, a means is disclosed whereby other parameter measuring transducer outputs, such as a temperature, can be utilized through appropriate circuitry to modulate the output of the implantable body transducer.

21 Claims, 6 Drawing Figures

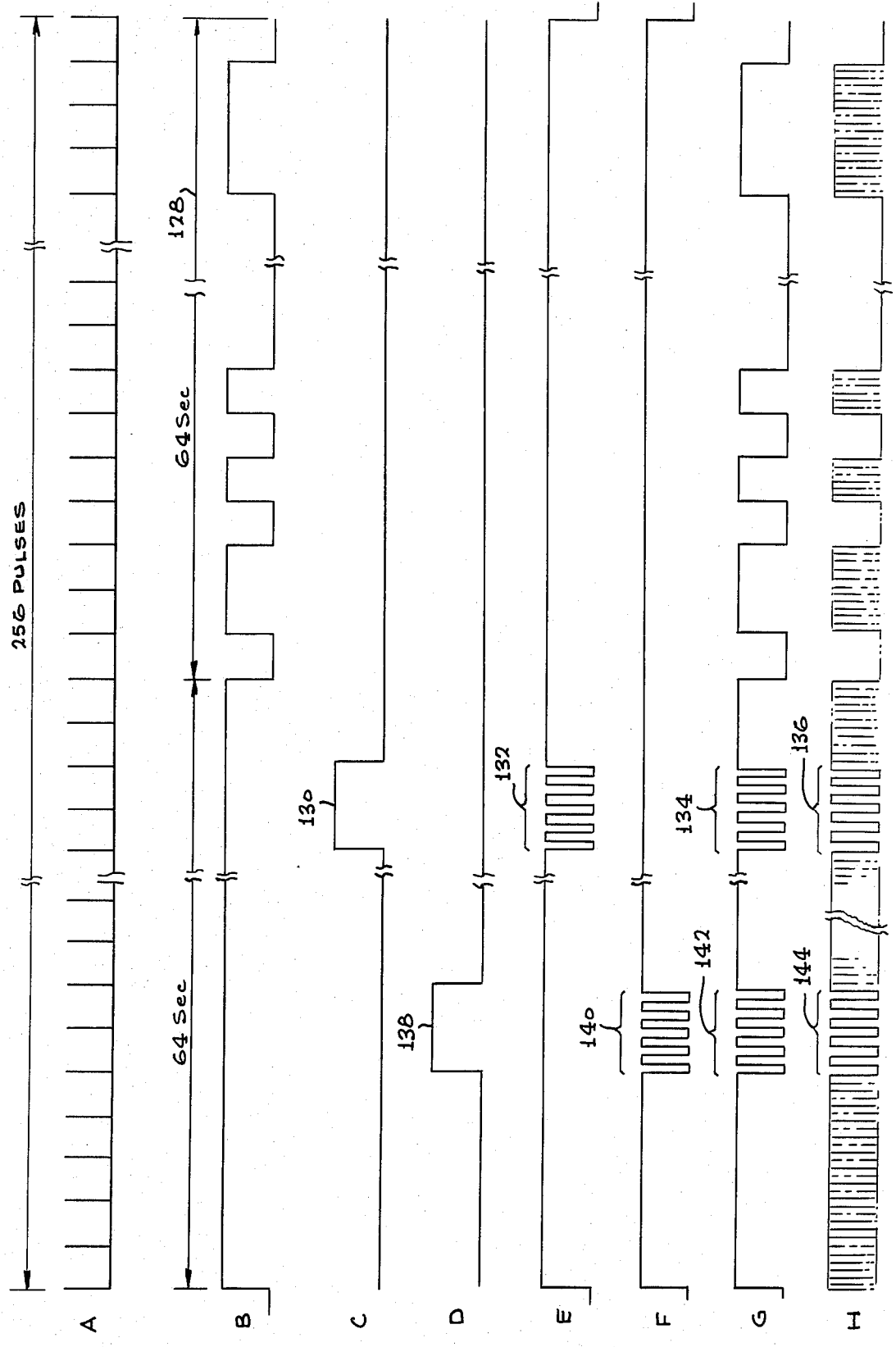

IMPLANTABLE CALIBRATION MEANS AND CALIBRATION METHOD FOR AN IMPLANTABLE BODY TRANSDUCER

FIELD OF THE INVENTION

The invention relates to transducers implantable in a body, and more particularly to transducers having a self-contained calibration means.

BACKGROUND OF THE INVENTION

Implantable body transducers have recently been utilized in the medical sciences. An example of such a transducer is a pressure measuring transducer for measuring dura pressure, pressure within the heart, and other fluid pressures at various locations throughout the body. A common type of pressure measuring transducer utilizes an L-C oscillator having a resonant circuit comprising a fixed L and a variable C. The variable C consists of a capacitor having a fixed capacitive electrode and a movable capacitive electrode in the form of a stiff pressure responsive diaphragm, the output frequency of the oscillator being a function of the pressure sensed by the diaphragm. Thus, as the pressure surrounding the transducer varies, the capacitance of the capacitor changes due to deflection of the movable capacitive electrode, thereby resulting in a change in the output frequency of the L-C oscillator. A signal related to the L-C oscillator output is inductively coupled to an external processing device which converts the received frequency to a pressure indication. A problem inherent with these systems has been obtaining an accurate calibration of capacitive change as a function of pressure variation. Since very small movements of the movable capacitive electrode are experienced as the fluid pressure changes, an accurate interpretation of the L-C oscillator output frequency as it relates to pressure changes is essential. This calibration requirement has been conventionally met in one of two possible ways. The first way has been to individually calibrate each of the variable C's during fabrication of the transducer, and then to provide calibration curves to the doctor implanting the transducer in a patient. One problem with this technique is that the transducer cannot be effectively utilized at a location remote from the implanting doctor's records. The second way, and one more commonly used, is for each manufacturer to standardize the characteristics of each of his transducers so that a single standardized calibration curve will apply to all of a specific transducer model. This technique has been employed to some success; however, the cost of modifying each variable capacitor to meet certain predetermined performance characteristics has proven to be very expensive and has raised the cost of the transducers considerably. An additional problem with this method is that the standardized curve still must be available to each doctor attempting to utilize the transducer. Another problem has been that calibration curves vary as a function of unknown internal variables such as temperature. Thus, there is a need to provide a calibration means for implantable pressure measuring transducers, and a means for monitoring internal variables, which is contained within and can be recovered from the transducer itself, and which will be immediately available to any doctor at any location in which the transducer is to be utilized. The present invention provides such a calibration means.

SUMMARY OF THE INVENTION

The present invention provides a calibration means which can be utilized in combination with an implantable body transducer. The calibration means includes a means for storing predetermined calibration data for the implantable transducer, a means for accessing the stored predetermined calibration data, and a means for generating a calibration output signal related to the stored predetermined calibration data. In addition, the invention provides a means whereby the calibration output signal can be used to modulate an output from the implantable body transducer. The invention also provides a means for monitoring internally varying parameters, such as temperature and power supply voltage, associated with performance of the implantable body transducer and a means for generating a signal related to these monitored internal parameters which can be transmitted to an external device. In an exemplary embodiment, the implantable body transducer is a pressure measuring transducer utilizing an L-C oscillator having a resonant circuit comprising a fixed L and a variable C, the variable C having a fixed capacitive electrode and a movable capacitive electrode in the form of a stiff pressure-responsive diaphragm, the output frequency of the oscillator being a function of the pressure sensed by the diaphragm. All that is needed external to the patient is a means for receiving and interpreting the predetermined calibration data and any other associated data such as temperature, this means being the same for all implantable body transducers of the same type and having a calibration means in accordance with the present invention. The predetermined calibration data is stored in a PROM having a plurality of digital storage elements, the storage elements being accessed or addressed by a counter in accordance with a predetermined sequence. The accessed storage elements determine the state of a serial bit stream utilized to digitally pulse-code modulate an output of the implantable body transducer.

In the exemplary embodiment, a first portion of the serial bit stream from the PROM provides a continuous output of the implantable body transducer, and a second portion provides a pulse code modulation of the transducer output which can be demodulated and processed by an external processing means, thereby developing an accurate calibration curve for the transducer. In accordance with an additional feature of the invention, the counter is chosen so that it will reinitiate a counting cycle any time that an inductively-coupled external power source for the transducer is deactivated for a predetermined time. Since the first portion of the PROM serial bit stream output provides for continuous output of the implantable transducer, periodic interruption of the external power source before initiation of the second portion of the serial bit stream can provide a means whereby the pulse code modulated calibration data need only be read once during a given measurement period. In addition, the invention discloses a means whereby other parameter-measuring transducers such as a temperature sensor, a power supply voltage sensor, or a calibration capacitor having a predetermined capacitance can be utilized to modulate the transducer output during predetermined time periods, thereby providing more data which can be used in conjunction with the pulse code modulated calibration data to provide an even more accurate calibration of the transducer.

The invention also provides a means whereby the frequency of the external power source is utilized to control a clock pulse generator within the implantable body transducer, the clock pulse generator controlling the counter utilized for addressing the digital storage elements within the PROM. By using this technique, the externally located processing means can also utilize the power source output to synchronize the incoming calibration data without having access to clock pulses generated within the implantable body transducer.

In addition, in an implantable body transducer for sensing a body-related parameter, and a means for generating a parameter output signal related to the parameter, the invention provides a method for calibrating the transducer comprising the steps of storing predetermined calibration data for the implantable body transducer in an implantable device, accessing the stored predetermined calibration data, and generating a calibration output signal related to the stored predetermined calibration data.

BRIEF DESCRIPTION OF THE DRAWINGS

FIG. 6 is a series of waveforms taken at various points in the block and schematic diagram of FIG. 5.

DETAILED DESCRIPTION

As required, a detailed illustrative embodiment of the invention is disclosed herein. This embodiment exemplifies the invention and is currently considered to be the best embodiment for such purposes. However, it is to be recognized that other types of implantable body transducers and other means for providing the stored predetermined calibration data to an external device could be utilized. Accordingly, the specific embodiment disclosed is representative in providing a basis for the claims which define the scope of the present invention.

As previously explained, the invention provides a calibration means whereby predetermined calibration data is stored within an implantable body transducer and is used to generate a calibration output signal which can be monitored by an external device. In an exemplary embodiment, the implantable body transducer is a pressure-measuring transducer utilizing an L-C oscillator having a resonant circuit comprising a fixed L and a variable C. The variable C has a fixed capacitive electrode and a movable capacitive electrode in the form of stiff pressure responsive diaphragm, the output frequency of the oscillator being a function of the pressure sensed by the diaphragm. The transducer output signal has a frequency related to the frequency of the L-C oscillator, this output frequency being used to determine the internal body pressure. The change in the L-C oscillator frequency as a function of pressure upon the movable capacitive electrode is stored as digital data within a plurality of digital storage elements contained within the transducer. At a predetermined time with respect to initiation of a pressure measurement, the digital data is accessed and used to modulate the L-C oscillator output, thereby providing a pulse-code modulated output which can be processed by an external processing means to accurately determine the pressure being experienced by the movable capacitive electrode. In addition, the calibration means provides for measurement of other environmental parameters such as temperature and power supply voltage which can be utilized to more accurately interrupt the stored calibration data. The stored calibration data could also contain calibration data for the temperature sensor and identification number for the specific implanted transducer being utilized, this data also being useful in providing a precise calibration for the implanted transducer. As an example, a thermistor for measuring temperature is used to modulate an oscillator which in turn modulates the L-C oscillator output during a predetermined time period with respect to initiation of a pressure measuring cycle, thereby providing an accurate determination of temperature in the vicinity of the pressure measuring transducer.

Figure 1:
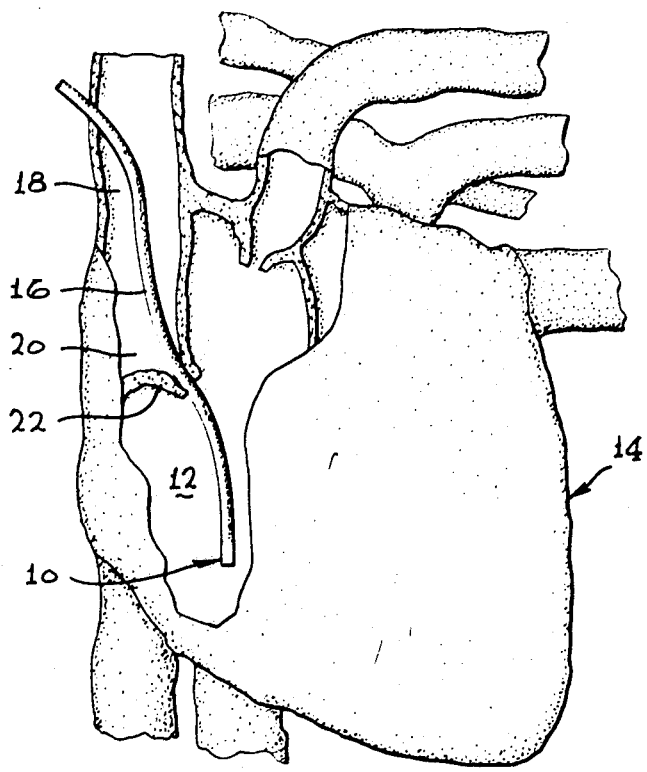
FIG. 1 is a schematic representation of a heart showing a pressure measuring transducer positioned therein.

Referring now to FIG. 1, an implantable body pressure measuring transducer 10 is shown positioned within the right ventricle 12 of a heart 14. It is attached to a flexible holding line 16 and inserted through the venae cavae 18, the right auricle 20, and the tricuspid valve 22. For each beat of the heart 14, pressure within the right ventricle 12 is sensed by the pressure measuring transducer 10, the results of this pressure sensing being transmitted by the pressure measuring transducer 10 to a receiver located externally to the body. Although the pressure measuring transducer 10 is shown in the right ventricle 12, it could equally well be placed in the left ventricle, the right auricle, or the left auricle. In addition, it could be located any place within a body where pressure measurements are to be made such as within the intestine or through a hole in the skull to measure brain pressure against the dura.

Figure 2:
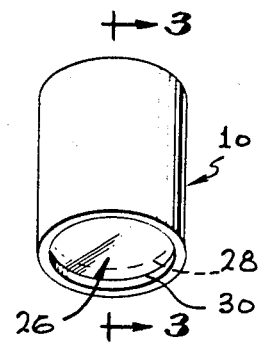
FIG. 2 is a perspective view of the pressure measuring transducer containing a calibration means according to the present invention.
Figure 3:
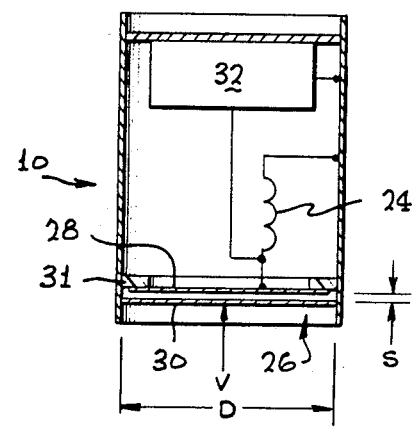
FIG. 3 is a cross-sectional view taken along lines 3—3 of FIG. 2 showing the L-C oscillator and associated electronics package in which is contained the calibration means according to the present invention.

In order to properly understand the exemplary embodiment, it is necessary to briefly describe the pressure sensitive transducer in which the calibration means is contained, and the characteristics of a pressure-sensitive capacitor which suggests a self-contained calibration means. Referring to FIGS. 2 and 3, the implantable body pressure measuring transducer 10 comprises an L-C oscillator having a resonance circuit which includes a fixed inductor (L) 24 and a variable capacitor (C) 26. The variable capacitor 26 has a fixed capacitive electrode 28 and a movable capacitive electrode 30 in the form of a stiff pressure responsive diaphragm, the output frequency of the oscillator being a function of the distance between the fixed capacitive electrode 28 and the movable capacitive electrode 30. The fixed capacitive electrode 28 is mounted on an insulating ring 31 so that it will be electrically isolated from the movable capacitive electrode 30. An electronics unit 32 is provided which contains circuitry comprising the calibration means according to the present invention as well as other circuitry utilized in conjunction with the pressure measuring transducer. In addition, the electronics unit contains a means for receiving and utilizing externally radiated energy to power the transducer, and radiation means whereby information developed by the pressure measuring transducer is transmitted to an external receiving unit. In a specific application, the movable capacitive electrode 30 has a diameter D of 0.75 inches and a spaced-apart distance S between the fixed capacitive electrode 28 and the movable capacitive electrode 30 of 1 to 2 milli-inches. The variable capacitor 26 and the fixed inductor 24 provide a resonant circuit whose output frequency as seen by the electronics unit 32 is determined by the capacitance of the variable capacitor 26. As fluid surrounding the pressure measuring transducer 10 inserts a pressure against the movable capacitive electrode 30 as shown by the vector V, the movable capacitive electrode 30 will be depressed inwardly towards the fixed capacitive electrode 28, thereby changing the resonant frequency of the inductor 24/capacitor 26 combination. An external receiving and processing unit can convert the output frequency of the pressure measuring transducer 10 to a corresponding pressure exerted by the vector V if the capacitance of the variable capacitor 26 as a function of pressure is accurately known.

Figure 4:
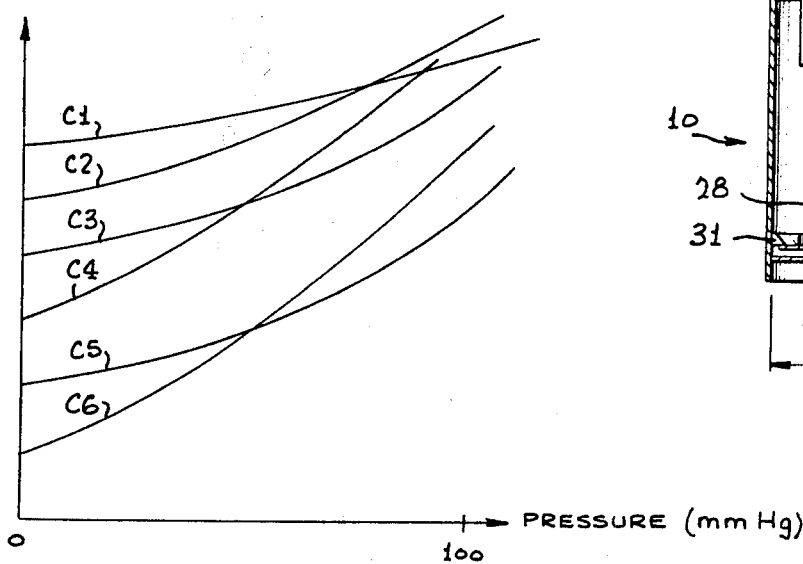
FIG. 4 is a qualitative representation of capacitance of a plurality of capacitors of the type used in an implantable pressure measuring transducer as a function of pressure on the movable capacitive electrode.

As has been previously explained, variable capacitors of the type utilized in an implantable body pressure measuring transducer 10 generally exhibit different capacitance versus pressure characteristics as qualitatively shown in FIG. 4. For a given pressure, a plurality of transducer capacitors as represented by $C_1$ through $C_6$ would provide different output frequencies. Thus, it is either necessary to know the specific capacitance vs. pressure characteristics of each variable capacitor, or to sufficiently control manufacture of each variable capacitor so that all will have the same capacitance versus pressure characteristics. The present invention provides a calibration means which can be located within each pressure measuring transducer so that pressure information provided by the transducer also includes the calibration information associated with the variable capacitor. Calibration information is broadly defined, and can include an identifying serial number for the specific transducer being utilized and calibration information for any other parameter measuring sensor utilized in conjunction with the pressure measuring transducer as will be explained below.

Figure 5:
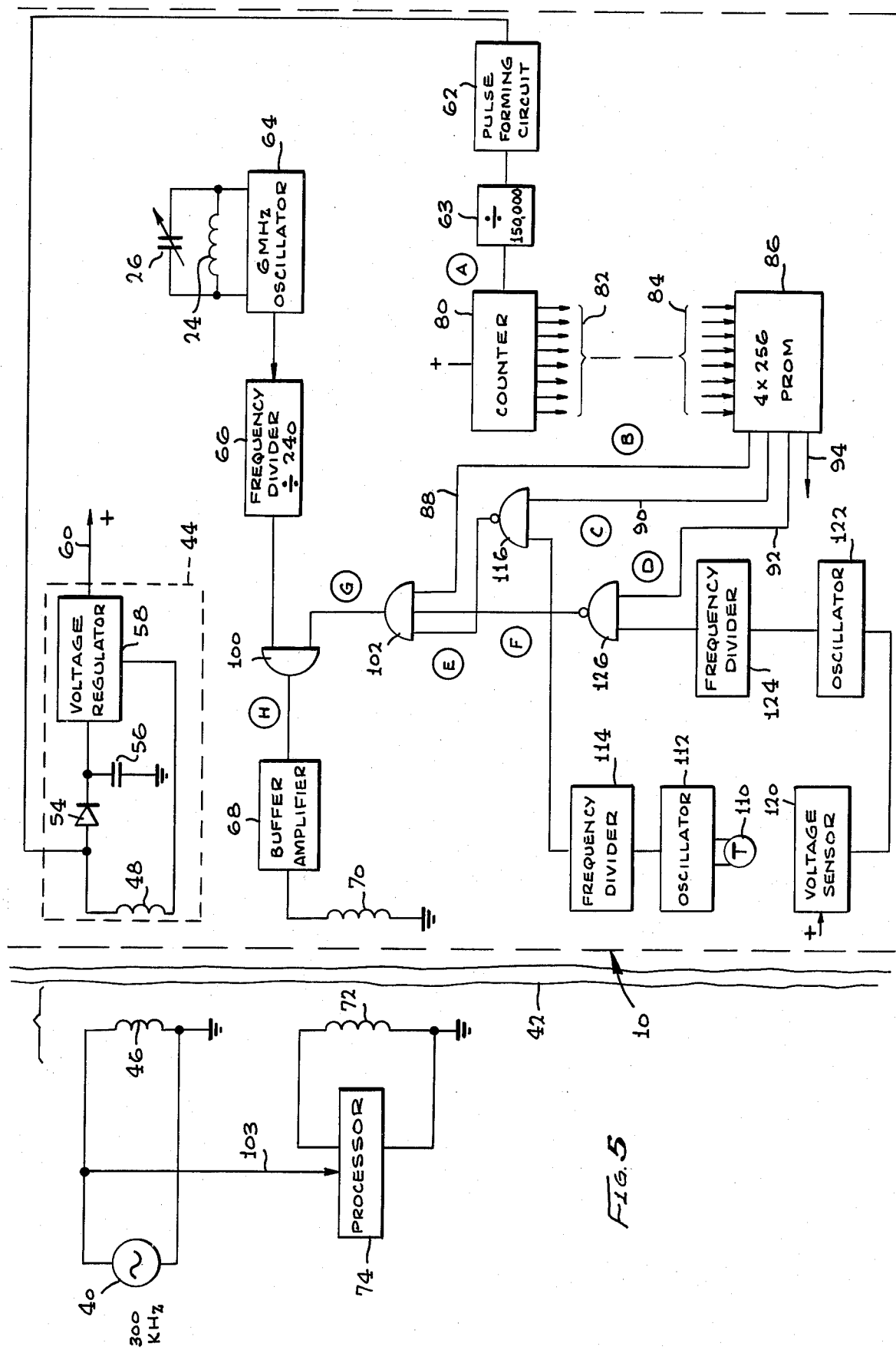
FIG. 5 is a block and schematic diagram of the calibration means according to the present invention.

The calibration means according to the present invention is shown in FIG. 5. A 300 KHz power source 40 is inductively coupled through the skin 42 of a patient to a power supply 44 contained within the pressure measuring transducer 10. However an implantable lithium battery could be used in lieu of the power supply 44. The transfer of power is effected by a power transmitting coil 46 and a power receiving coil 48 in the implantable pressure measuring transducer 10. The power supply 44 is constructed so that power received by the power receiving coil 48 is rectified by a rectifying diode 54 and a smoothing capacitor 56 to provide a DC input to a voltage regulator 58 which in turn provides a regulated DC output voltage on a voltage output line 60. The DC output voltage is used to power the various elements of the pressure measuring transducer 10. In addition, the unrectified 300 KHz received signal is also provided to a pulse forming circuit 62 which, in conjunction with a divide by 150,000 circuit 63, provides output clock pulses for synchronization of the calibration means as will be explained in detail below.

The basic pressure measuring transducer 10 comprises the variable capacitor 26 and fixed inductor 24 connected in parallel, the combination being connected to circuitry which comprises an oscillator 64 having a nominal frequency of a 6 MHz. The output of the 6 MHz oscillator 64 is provided to a frequency divider 66 which provides an output signal having a nominal frequency of 25 KHz by dividing the 6 MHz signal by 240. The frequency divider could also be a frequency multiplier if a higher output frequency is desired. The output of the frequency divider 66 is provided to a buffer amplifier 68 which in turn provides the nominal 25 KHz signal to a data transmitting coil 70. The data transmitting coil 70 is inductively coupled to a data receiving coil 72 which provides a data input to a processor 74. The processor 74 converts the signal frequency received from the data receiving coil 72 to a pressure differential experienced by the variable capacitor 26.

Th divide by 150,000 circuit 63 is chosen so that it converts 300 KHz pulses from the pulse forming circuit 62 to a clock pulse signal having 2 pulses per second. A counter 80 is provided which has eight binary output lines 82 which define $2^8$ or 256 discrete outputs. A counting cycle is defined by sequentially stepping through all of the 256 discrete outputs. The counter 80 is configured, for reasons to be explained below, so that it will be reset whenever voltage is removed from line 60 and a new counting cycle initiated when voltage is returned to line 60. The eight binary output lines 82 from the counter 80 comprise eight input lines 84 to a 4 by 256 programmable read only memory (PROM) 86, the 4 referring to the number of memory planes and associated output lines from the PROM and the 256 referring to the number of digital storage elements within each memory plane. PROM's suitable for this application include an Intersil Co. chip 6603 (4X1000) or chip 6604 (8X512). Harris Co. manufactures a 4X256 chip No. 6611.

At this point it will be helpful to explain operational characteristics of the PROM 86 and its application to the calibration means of the present invention. Referring to the first memory plane of the PROM 86, it is well understood by those familiar with the digital processing art that the PROM can be programmed so that each of the 256 digital storage elements contains either a 1 or a 0. Once the storage elements have been programmed, they are burned in so that the programmed 1's or 0's become fixed within the PROM. Having programmed the 256 storage elements, the PROM is constructed so that each storage element can be addressed in accordance with which of the 256 possible discrete outputs from the counter 80 is present on the PROM input lines 84. Thus, for the first memory plane within the PROM 86, if the input lines 84 all contain 0's, and the first digital storage element is programmed with a 1, a signal corresponding to a 1 will appear on a first PROM output line 88. When the counter 80 steps to the next discrete output, the second digital storage element within the first memory plane will be addressed. If that digital storage element is also programmed with a 1, then the first PROm output line 88 will continue to have a signal corresponding to a 1 appear thereon. However, if the second digital storage element is programmed with a 0, then when that storage element is addressed the first PROM output line 88 will have a signal corresponding to a 0 appear on it. Thus, as one can appreciate, as the counter 80 cycles through the 256 possible discrete outputs, each of the 256 digital storage elements in the first memory plane will be sequentially addressed and connected to the first PROM output line 88, and the signal appearing on that line during the first counting cycle will appear as a serial bit train comprising 256 bits, each individual bit corresponding to a 1 or 0 in accordance with the 1's or 0's programmed into the first memory plane. In a corresponding manner, and for purposes for which will be explained in more detail below, each digital storage element in the three remaining memory planes of the PROM 86 is also simultaneously addressed as its corresponding digital storage element in the first memory plane is addressed. Each memory plane is connected to a corresponding PROM output line. Thus the second memory plane is connected to a second PROM output line 90, the third memory plane to a third PROM output line 92, and the fourth memory plane to a fourth PROM output line 94. Therefore, the 4 by 256 PROM 86 has four output lines each containing a serial bit stream having a predetermined relationship to the other three bit streams on the other three output lines. For the exemplary embodiment being described, a 4 by 256 PROM has been chosen. However, other PROM configurations could also be utilized such as a 4 by 1000 PROM, an 8 by 512 PROM, etc.

Continuing now in reference to FIG. 5, an output control gate 100 is provided, the output gate 100 having as one input the output of the frequency divider 66 and as another input a gate control signal provided by a modulation gate 102. An output from the modulation gate 102 corresponding to a 1 allows the output from the frequency divider 66 to pass directly to the buffer amplifier 68. An output from the modulation gate 102 corresponding to a 0 results in the output control gate 100 blocking an output from the frequency divider 66. Thus one can appreciate that by appropriately controlling the output of the modulation gate 102, the output from the frequency divider 66 can be pulse modulated in accordance with various inputs to the modulation gate 102. Based upon the above, it should now be apparent that if all the inputs to the modulation gate 102 are high, the output of the frequency divider 66 will be impressed across the data transmitting coil 70. However, if any of the inputs to the modulation gate 102 are low, then the output of the frequency divider will not appear across the data transmitting coil 70. Assuming for the moment that the only input to the modulation gate 102 is the serial bit stream appearing on the first PROM output line 88, then it can be appreciated that if some of the PROM digital storage elements in the first memory plane are programmed with 1's and 0's in accordance with predetermined calibration data, then that calibration data will appear as pulse modulation on the output signal appearing across the data transmitting coil 70. Since the serial bit stream on the first PROM output line 88 is synchronized to the 300 KHz source 40 by the pulse forming circuit 62 and the divide by 150,000 circuit 63, then in accordance with an additional feature of the invention it is possible to synchronize the pulse modulated signal received by the processor 74 with the power source 40 without having access to the clock pulses provided by the divide by 150,000 circuit 63. An interconnection line 103 is provided to effect this synchronization.

In accordance with another feature of the invention, a temperature sensor 110, which could be a thermistor, is located within the pressure measuring transducer 10 so that it can measure the temperature of the surrounding fluid. The output of the temperature sensor 110 controls the output frequency of an associated oscillator 112 whose output is divided by an associated frequency divider 114 so that a nominal output frequency corresponding to an expected temperature would be approximately 150 Hz. This 150 Hz signal is supplied to a temperature sensor NAND gate 116. The second memory plane of the PROM 86 is programmed so that the serial bit stream appearing on the second PROM output line 90 will be high (i.e. 1's) only at a time in the counting cycle during which it is desired to measure the temperature of the surrounding fluid. If any of the inputs to the temperature sensor NAND gate 116 are low, its output will be high and provide a high input to the modulation gate 102. However, if the serial bit stream on the second PROM output line 90 is high, the output from the temperature sensor frequency divider 114 will modulate the output from the temperature sensor NAND gate 116. As long as the other inputs to the modulation gate 102 are high, then the modulated output from the temperature sensor NAND gate 116 will cause an identical modulation to appear on the output line of the modulation gate 102. This identical modulation will in turn modulate the output of the frequency divider 66 by controlling operation of the output control gate 100. Thus, a nominal 150 Hz output signal from the temperature sensor frequency divider 114 will be modulated on the 25 KHz output signal from the frequency divider 66, the precise modulation frequency being related to the temperature being experienced by the temperature sensor 110.

In a similar manner, a voltage sensor 120 is also provided to measure the regulated output voltage of the power supply 44. The output of the voltage sensor 120 is utilized to control the frequency of an associated oscillator 122 whose output frequency is again lowered by an associated frequency divider 124. The output of the voltage sensor frequency divider 124 again supplies one input to a voltage sensor NAND gate 126, the other input being the serial bit stream on the third PROM output line 92. The third memory plane of the PROM 86 is thus programmed so that the digital storage elements corresponding to a time period when the voltage sensor data is desired are programmed with 1's as explained with respect to the temperature sensor 110. In a similar manner although not shown, a third environment sensing element such as a calibration capacitor or a ph sensor could be used in conjunction with the fourth PROM output line 94 as previously explained for the temperature sensor 110 and the voltage sensor 120.

In order to standardize circuitry contained within the pressure measuring transducer 10, the oscillators 112 and 122 and frequency dividers 114 and 124 can be identical to each other because the time in which their respective outputs modulate the output of the frequency divider 66 can be determined in accordance with an activation time of the 300 KHz power source 40 as previously explained, or in accordance with the beginning of each counting cycle of the counter 80. The latter can be determined by programming the first few digital storage elements of the first PROM memory plane with some type of synchronization code.

Operation of the system can be understood by referring to the waveforms of FIG. 6 in conjunction with the block diagram of FIG. 5. Waveform A comprises the output of the divide by 150,000 circuit 63 which consists of clock pulses occurring at a rate of 2 per second, each pulse resulting in the counter 80 stepping to the next of its 256 possible discrete outputs. The serial bit stream on the first PROM output line 88 is shown in Waveform B and consists of 64 seconds of a high output and then 64 seconds of calibration data. The second 64 seconds as shown at 128 can be coded in many different ways to provide three or more points from which a calibration curve for the variable capacitor 26 can be derived. This calibration data should be formatted in accordance with a software program provided for the processor 74. Thus, an accurate calibration curve for the implantable pressure measuring transducer can be derived at any remote processing site if it has the appropriate software program. It is not necessary, as with conventional implanted transducers, for each processing site to have a calibration curve on file for each individual transducer. Thus, if only predetermined calibration data is desired, an output of the modulation gate 102 will be as shown in waveform B in which during the first 64 seconds the output o the frequency divider 66 is applied directly to the buffer amplifier 68, and then during the second 64 seconds as shown at 128, the output of the frequency divider is pulse-code modulated before being applied to the buffer amplifier 68.

If additional data from the transducer and its surrounding environments are desired, the waveforms will be as shown in C through H of FIG. 5. The serial bit stream from the second PROM memory plane is provided on the second PROM output line 90 as shown in waveform C. The second PROM memory plane is programmed so that the serial bit stream will be high only during the time period as shown at 130. The waveform C bit stream comprises an input to the temperature sensor NAND gate 116, the other input being the output of the temperature sensor frequency divider 114. Thus, during the period the serial bit stream on the second PROM output line 90 is high, the output of the temperature sensor NAND gate 116 will be as shown in waveform E, the output being modulated as shown at 132 in accordance with the frequency of the output signal from the temperature sensor frequency divider 114. As can be seen, during this period the output on the first PROM output line 88 is high, thereby allowing the modulation occurring at 132 on waveform E to be duplicated in the output of the modulation gate 102 as shown at 134. This modulation then controls the output control gate 100, thereby modulating the output from the frequency divider 66 as shown at 136. In a similar manner, if data from a second sensor is desired, the serial bit stream from the third PROM memory plane is provided on the third PROM output line 92 as shown in waveform D at 138. Again, as explained in conjunction with the temperature sensor, when waveform D as shown at 138 goes high, modulation from the voltage sensor frequency divider 124 output results in modulation of the voltage sensor NAND gate 126 output as shown in waveform F at 140. This NAND gate 126 output, since waveforms E and B are high at this time, modulates the output of the modulation gate 102 as shown in waveform G at 142, which in turn modulates the output of the frequency divider 66 as shown at 144. Thus, the calibration means of the present invention provides as an output signal the waveform shown at H in FIG. 6 which contains sufficient information to determine the frequency of the 6 MHz oscillator 64 and the measurements from a plurality of environment-sensing transducers.

In accordance with an additional feature of the invention, the 300 KHz power source 40 can be controlled so that its power output will be momentarily interrupted every 60 seconds. This interruption will cause the counter 80 to reinitiate a counting cycle so that the output appearing across the data transmitting coil 70 will be only the first 60 seconds of the output waveform shown at H, thereby eliminating the pulse modulated portion relating to the predetermined calibration data. This elimination may be desirable in some using situations since the predetermined calibration data is only needed once during a pressure-measuring session. However, it may be desirable to continually monitor temperature and pressure as shown at 144 and 146.

It should now be apparent that a calibration means has been described whereby predetermined calibration data as well as data from other parameter sensing transducers can be obtained from an implantable body transducer.

What is claimed is:

1. In combination with an implantable body transducer for sensing a body-related parameter, and a means for generating a parameter output signal related to said body-related parameter, an implantable calibration means for said transducer comprising:
   means for storing predetermined calibration data for said implantable body transducer;
   means for accessing said stored predetermined calibration data; and
   means for generating a calibration output signal related to said stored predetermined calibration data.

2. The calibration means of claim 1 in which said storing means comprises a first plurality of digital storage elements having 1's or 0's in accordance with said predetermined calibration data.

3. The calibration means of claim 2 in which said accessing means comprises means for sequentially addressing said first plurality of digital storage elements and said first plurality of digital storage elements comprise a PROM having an input responsive to said sequentially addressing means and a first output comprising a serial bit stream forming 1's and 0's corresponding to said 1's and 0's programmed in said first plurality of digital storage elements.

4. The calibration means of claim 3 in which said sequentially addressing means comprises a counter having a plurality of digital outputs each of which corresponds to one of said first plurality of digital storage elements.

5. The calibration means of claim 4 in which said implantable body transducer is powered by an inductively coupled energizer having a predetermined frequency, further comprising means for controlling occurrences of said counter digital outputs in proportion to said energizer predetermined frequency, the occurrence of each of said plurality of digital outputs comprising a counting cycle.

6. The calibration means of claim 5 in which said counter comprises means to reinitiate a counting cycle when power is removed from said counter.

7. The calibration means of claim 4 further comprising first means for modulating said parameter output signal by said calibration output signal.

8. The calibration means of claim 7 further comprising:
   a first sensor;
   a first sensor oscillator having an output frequency related to a parameter measured by said first sensor; and
   second means for modulating said parameter output signal by said first sensor oscillator output.

9. The calibration means of claim 8 in which said PROM comprises a second plurality of digital storage elements programmed with 1's or 0's in accordance with a first predetermined time period during which said parameter outut signal is to be modulated by said first sensor oscillator output, said PROM having a second output comprising a second serial bit stream forming 1's and 0's corresponding to said 1's and 0's stored in said second plurality of digital storage elements, said second plurality of digital storage elements each being addressed as each of said first plurality of digital storage elements is addressed by said counter, said calibration means further comprising means for modulating said parameter output signal by said first sensor oscillator output only during said first predetermined time period defined by said second serial bit stream.

10. The calibration means of claim 9 in which said implantable body transducer is a pressure measuring transducer and said first sensor is a temperature sensor.

11. The calibration means of claim 9 further comprising
   a second sensor;
   a second sensor oscillator having an output frequency related to a parameter measured by said second sensor; and
   third means for modulating said parameter output signal by said second sensor oscillator output.

12. The calibration means of claim 11 in which said PROM comprises a third plurality of digital storage elements programmed with 1's or 0's in accordance with a second predetermined time period during which said parameter output signal is to be modulated by said second sensor oscillator output, said PROM having a third output comprising a third serial bit stream forming 1's and 0's corresponding to said 1's and 0's stored in said third plurality of digital storage elements, said third plurality of digital storage elements each being addressed as each of said first plurality of digital storage elements is addressed by said counter, said calibration means further comprising means for modulating said parameter output signal by said second sensor oscillator output only during said second predetermined time period defined by said third serial bit stream.

13. The calibration means of claim 11 in which said second sensor is a voltage sensor.

14. The calibration means of claim 1 further comprising:
   a first sensor; and
   means for generating an output signal related to a parameter measured by said first sensor.

15. In combination with an implantable body pressure measuring transducer utilizing an L-C oscillator having a resonant circuit comprising a fixed L and a variable C, the variable C having a fixed capacitive electrode and a movable capacitive electrode in the form of a stiff pressure responsive diaphragm, the frequency of said oscillator output signal being a function of the pressure sensed by said diaphragm, an implantable calibration means comprising:
   means for storing predetermined digital calibration data for said variable C; and
   means for modulating a signal related to said L-C oscilltor output signal by said stored predetermined digital calibration data.

16. The calibration means of claim 15 further comprising:
   an environment-sensing transducer and an associated oscillator; and
   means for modulating said L-C oscillator output by said associated oscillator.

17. The calibration means of claim 16 in which said environment-sensing transducer is a temperature sensor.

18. In an implantable body transducer for sensing a body-related parameter, and a means for generating a parameter output signal related to said parameter, a method for calibrating said transducer comprising the steps of:
   storing predetermined calibration data for said implantable body transducer in an implantable device;
   accessing said stored predetermined calibration data; and
   generating a calibration output signal related to said stored predetermined calibration data.

19. The method of claim 18 further comprising the step of modulating said parameter output signal by said generated calibration output signal.

20. The method of claim 19 further comprising the steps of:
   measuring a parameter associated with calibration of said implantable body transducer;
   modulating an oscillator by a signal related to said measured parameter; and
   modulating said parameter output signal by said oscillator output.

21. The method of claim 20 in which said implantable body transducer is a pressure-measuring transducer and said parameter associated with calibration of said implantable body transducer is temperature.

* * * * *